(12) United States Patent
Takahashi et al.

(10) Patent No.: US 8,758,258 B2
(45) Date of Patent: Jun. 24, 2014

(54) BEAT DETECTION DEVICE AND BEAT DETECTION METHOD

(75) Inventors: Yusuke Takahashi, Nagano (JP); Osamu Urano, Nagano (JP); Masao Kuroda, Nagano (JP)

(73) Assignee: Seiko Epson Corporation, Tokyo (JP)

(*) Notice: Subject to any disclaimer, the term of this patent is extended or adjusted under 35 U.S.C. 154(b) by 684 days.

(21) Appl. No.: 12/684,406

(22) Filed: Jan. 8, 2010

(65) Prior Publication Data

US 2010/0198087 A1    Aug. 5, 2010

(30) Foreign Application Priority Data

Feb. 2, 2009 (JP) ................. 2009-021236

(51) Int. Cl.
    *A61B 5/02*        (2006.01)
(52) U.S. Cl.
    USPC .......................................... 600/483; 600/503
(58) Field of Classification Search
    USPC .................... 600/481, 483–485, 490–503
    See application file for complete search history.

(56) References Cited

U.S. PATENT DOCUMENTS

| | | | | |
|---|---|---|---|---|
| 2002/0181698 | A1* | 12/2002 | Takahashi et al. | 379/406.01 |
| 2004/0249302 | A1* | 12/2004 | Donoghue et al. | 600/544 |
| 2005/0143634 | A1* | 6/2005 | Baker et al. | 600/310 |
| 2008/0275349 | A1* | 11/2008 | Halperin et al. | 600/484 |
| 2009/0005695 | A1* | 1/2009 | Kosuda et al. | 600/500 |

FOREIGN PATENT DOCUMENTS

| | | |
|---|---|---|
| JP | 06-098863 A | 4/1994 |
| JP | 11-276448 A | 10/1999 |
| JP | 2001-8908 A | 1/2001 |
| JP | 2002-224055 A | 8/2002 |
| JP | 2007-512043 A | 5/2007 |
| WO | 2005/046431 A2 | 5/2005 |

* cited by examiner

*Primary Examiner* — Michael Kahelin
*Assistant Examiner* — Yunqing Wang
(74) *Attorney, Agent, or Firm* — Global IP Counselors, LLP

(57) ABSTRACT

A beat detection device includes: a pulse wave sensor adapted to detect and output a pulse wave signal; a body motion sensor adapted to detect and output a body motion signal due to a body motion of a human body; a pulse wave signal filtering section adapted to generate an adaptive filter based on the body motion signal to extract a noise signal in the pulse wave signal, and to output a beat signal obtained by eliminating the noise signal from the pulse wave signal; and a filter coefficient setting section adapted to set a coefficient of the adaptive filter to be a predetermined value in response to detection of increase in a body motion change beyond a predetermined threshold value based on the body motion signal.

11 Claims, 16 Drawing Sheets

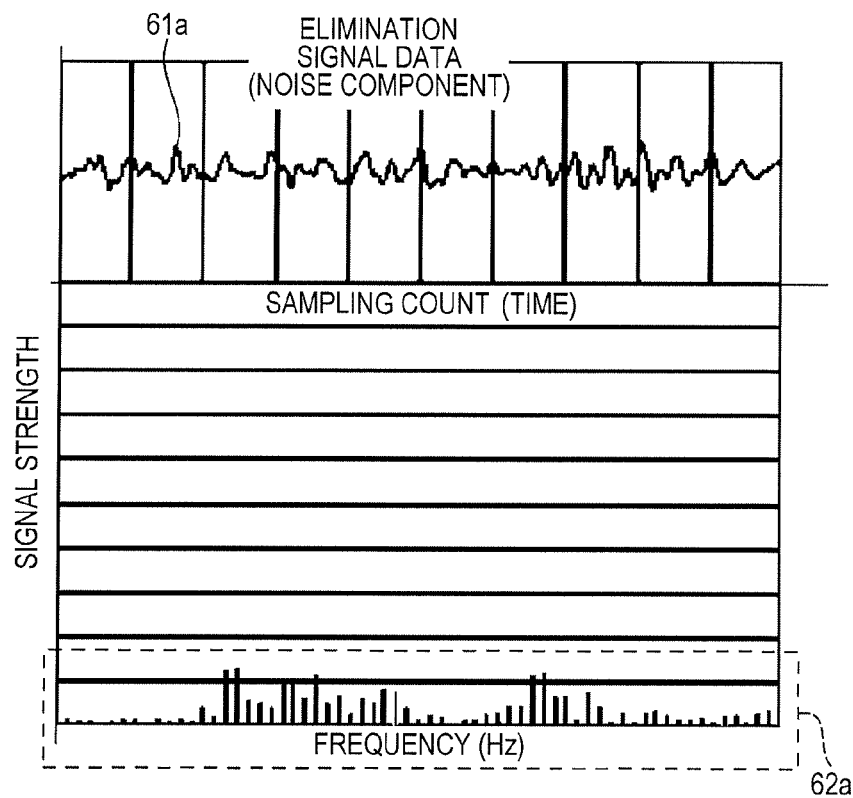
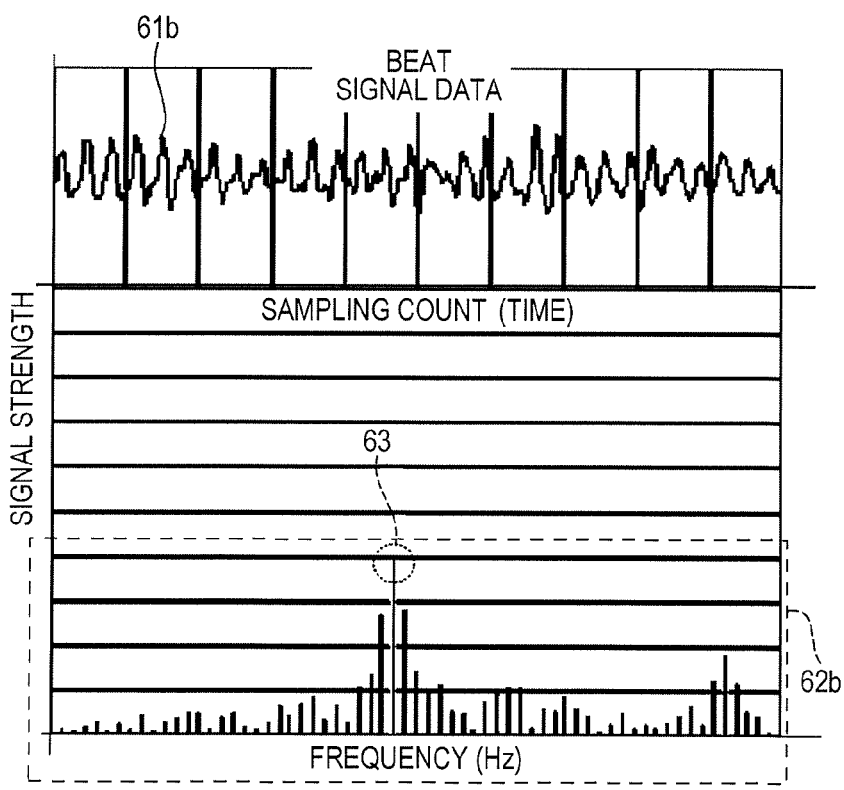

BEAT DETECTION DEVICE AND BEAT DETECTION METHOD

BACKGROUND

1. Technical Field

The present invention relates to a technology for detecting the beat of a human body, and in particular to a beat detection device and a beat detection method used in a state of being attached to the human body, and for detecting the beat in the body motion with accuracy.

2. Related Art

The beat detection device is a device for detecting the beat derived from the heartbeat of a human body, and specifically a device for eliminating, as a noise, a signal component (a body motion-sensitive signal) caused under the influence of the motion of the human body from a signal (a pulse wave signal) obtained from a pulse wave sensor attached to, for example, an arm or a finger, thereby detecting only the signal (the beat signal) derived from the heartbeat. Further, JP-A-2001-8908 and JP-A-2002-224055, for example, describe the technology of detecting the body motion signal using an acceleration sensor, and at the same time generating an adaptive filter referring to the body motion signal, thereby eliminating the body motion-sensitive signal from the pulse wave signal including the body motion-sensitive signal using the adaptive filter.

In the beat detection device of the related art, there is a problem that the beat signal cannot be detected accurately when the body motion rapidly varies so as to increase the momentum, for example, when a human in a resting state rapidly starts to walk, or when a human in a walking state rapidly starts to run.

SUMMARY

An advantage of some aspects of the invention is to provide a beat detection device capable of detecting the pulse wave accurately even in the case in which a human wearing the beat detection device changes the body motion rapidly so as to increase the momentum.

According to a first aspect of the invention, there is provided a beat detection device adapted to detect a beat signal derived from a beat of a human body, including a pulse wave sensor adapted to detect and output a pulse wave signal having the beat signal and a noise signal mixed with each other, a body motion sensor adapted to detect and output a body motion signal due to a body motion of the human body, a pulse wave signal filtering section adapted to generate an adaptive filter based on the body motion signal to extract the noise signal in the pulse wave signal, and to output the beat signal obtained by eliminating the noise signal from the pulse wave signal, and a filter coefficient setting section adapted to set a coefficient of the adaptive filter to be a predetermined value in response to detection of increase in a body motion change beyond a predetermined threshold value based on the body motion signal.

Further, according to another aspect of the invention, there is provided a beat detection method for detecting the beat signal derived from the beat of the human body including the steps of providing a computer provided with a pulse wave sensor adapted to detect the pulse wave signal having the beat signal and the noise signal mixed with each other and the body motion sensor adapted to detect and output the body motion signal due to the body motion of the human body, generating an adaptive filter based on the body motion signal to extract the noise signal in the pulse wave signal, and outputting the beat signal obtained by eliminating the noise signal from the pulse wave signal, and setting a coefficient of the adaptive filter to be a predetermined value in response to detection of increase in a body motion change beyond a predetermined threshold value based on the body motion signal.

BRIEF DESCRIPTION OF THE DRAWINGS

The invention will now be described with reference to the accompanying drawings, wherein like numbers reference like elements.

FIGS. 10A and 10B are diagrams respectively showing the elimination signal data and the beat signal data extracted by the beat detection process of the first embodiment described above.

DESCRIPTION OF EXEMPLARY EMBODIMENTS

Features of Aspects of Invention

Figure 1:
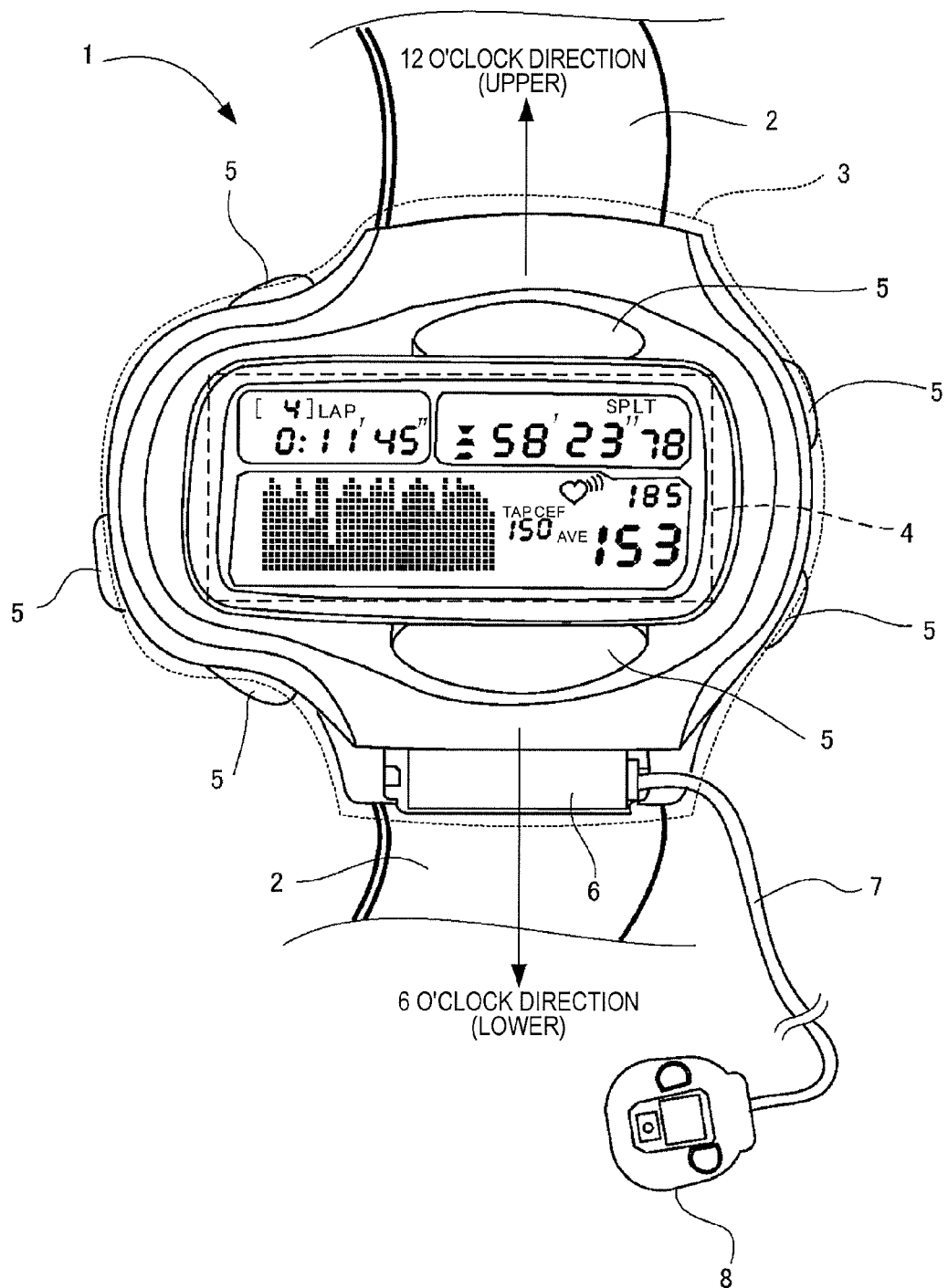
FIG. 1 is an appearance diagram of a wristwatch pulse meter as an embodiment of the invention.

In addition to the principal aspects of the invention described above, other aspects of the invention will hereinafter be revealed in the present specification. Features of the other aspects of the invention will be recited as follows.

The filter coefficient setting section resets the coefficient of the adaptive filter to be an initial value.

The beat detection device includes a body motion storage section adapted to store the body motion signal, which is detected before and after a predetermined body motion change, in correspondence with the coefficient of the adaptive filter, and the filter coefficient setting section sets, in response to detection of increase in the body motion change beyond the predetermined threshold value, and the body motion change corresponding to the predetermined body motion change, the coefficient of the adaptive filter to be a value corresponding to the body motion change.

The body motion sensor individually outputs body motion signals based on body motions in at least two axial directions, respectively, and the pulse wave signal filtering section sets the beat signal, which is based on a first pulse wave signal output by the pulse wave sensor and a body motion signal in an axial direction having a most significant influence on the first pulse wave signal, as a second pulse wave signal, and outputs the beat signal based on the second pulse wave signal and a body motion signal having a second most significant influence.

Further, if the beat detection device adapted to individually output the body motion signals based on the body motions in at least two axial directions, respectively, is used in the state of being attached to the arm, the body motion sensor sets a direction from a wrist toward an elbow as the axial direction having the most significant influence, and when extending the arm in parallel to a ground and setting a palm connected to the arm to be parallel to the ground, sets a direction perpendicular to both of that direction and the ground as the axial direction having the second most significant influence.

The filter coefficient setting section detects the increase in the body motion change beyond the predetermined threshold value based on a signal obtained by applying a band-pass filter on the body motion signal. Alternatively, the filter coefficient setting section detects the increase in the body motion change beyond the predetermined threshold value based on a summed value of the body motion signal output in a past predetermined period. Alternatively, the filter coefficient setting section detects the increase in the body motion change beyond the predetermined threshold value based on an amplitude of the body motion signal output in a past predetermined period.

The filter coefficient setting section stops, when setting the coefficient of the adaptive filter, setting the coefficient of the adaptive filter until a predetermined period of time elapses.

The beat detection device includes a pulse measurement section adapted to measure a pulse rate based on the beat signal, and a display section adapted to display the pulse rate.

Beat Detection Devices as Embodiment

As an embodiment of the invention, a wristwatch pulse meter will be cited. FIG. 1 shows an appearance diagram of the pulse meter 1. The pulse meter 1 has an appearance similar to a typical digital wristwatch, and is provided with a wristband 2, and a liquid crystal display (LCD) 4 for displaying various information such as time and a pulse rate using characters and numbers disposed on a front face of a case 3. Further, in the periphery of the case 3 and a frame portion of the front face of the case 3, there are disposed various buttons 5 for operating the pulse meter 1.

Here, as shown in the drawing, assuming the 12 o'clock direction of the watch in the state in which the numbers of the watch are displayed in an erected manner is an upper side, a detachable connector 6 is mounted on a lower side of the case 3. Further, internal contacts of the connector 6 are connected to an electronic circuit disposed inside the case 3 via contacts provided to the case 3.

Further, a cable 7 connected to the internal contacts of the connector 6 is guided to the outside of the connector 6, and a pulse wave sensor 8 is connected to the tip of the cable 7. Thus, the signal (the pulse wave signal) from the pulse wave sensor 8 is input to the electronic circuit disposed inside the case 3 via the cable 7 and the connector 6.

Figure 2:
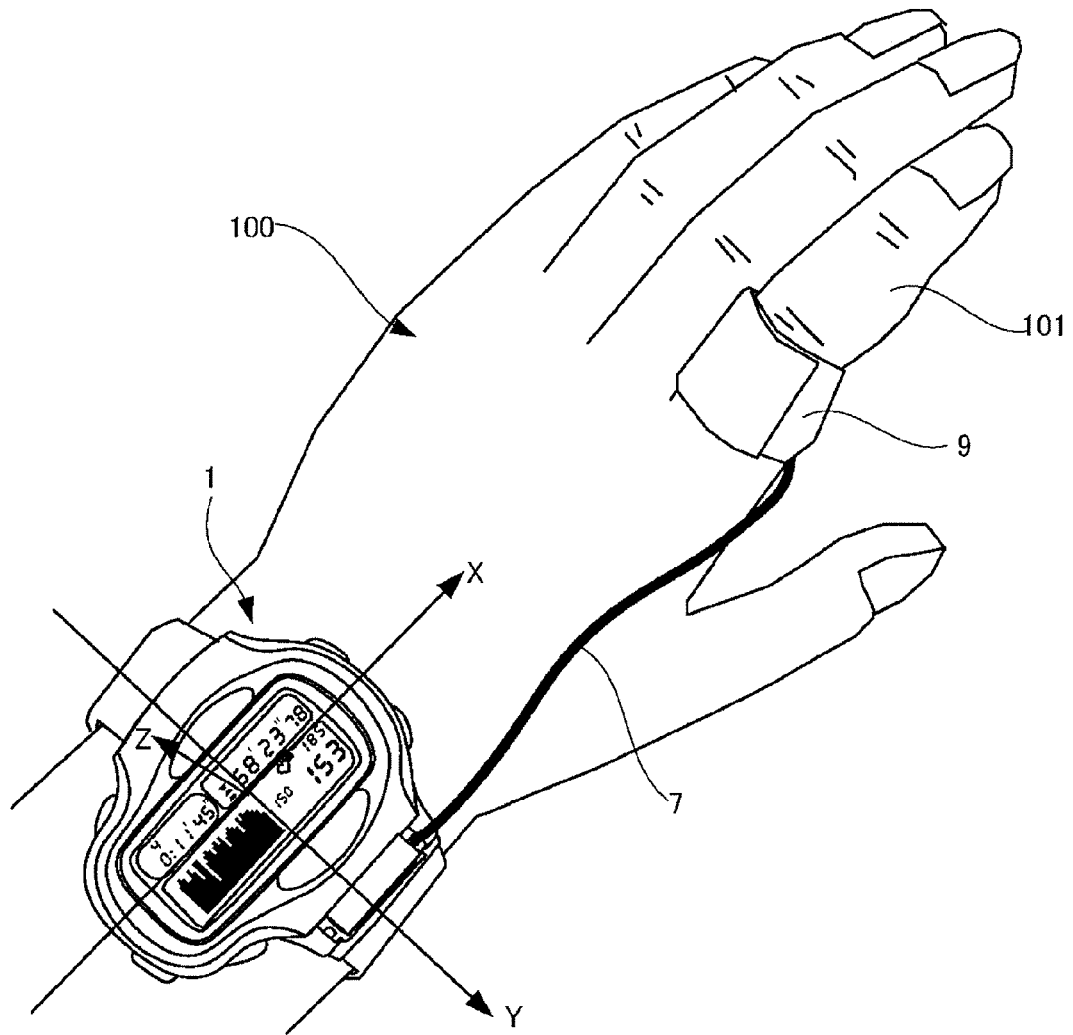
FIG. 2 is a diagram showing a state of wearing the pulse meter described above.

The pulse meter 1 is used for detecting the beat of the wearer while, for example, the wearer is walking or jogging, and then outputting the pulse rate based on the beat thus detected to display on an LCD 4, thereby presenting it to the wearer. FIG. 2 shows the state in which the pulse meter 1 described above is attached to a left hand 100 so that the pulse can be measured. In this drawing, the pulse wave sensor 8 is fixed by a supporter 9 wound around the finger 101 in the state of having contact with the finger 101. It should be noted that as the pulse wave sensor 8, there can be adopted an optical sensor provided with a light source and a light receiving sensor for an infrared ray or visible light and for detecting the pulse wave using the absorption characteristic of hemoglobin, a piezoelectric sensor for detecting the pulse wave as vibrations, or the like.

Configuration of Beat Detection Device

Figure 3:
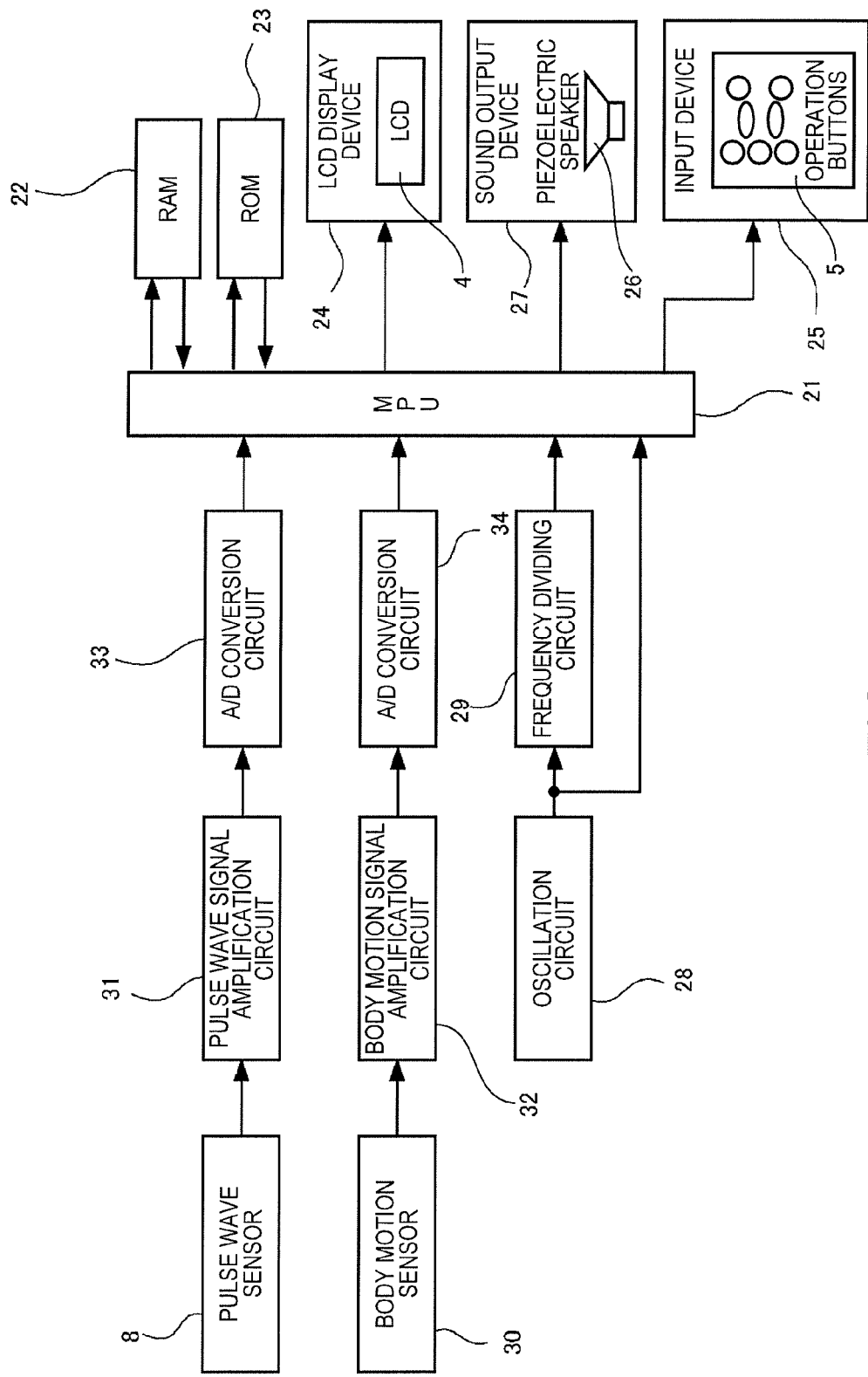
FIG. 3 is a functional block diagram of the pulse meter described above.

FIG. 3 shows the hardware configuration of the electronic circuit incorporated in the case 3 of the pulse meter 1 described above in the form of a block diagram. The hardware configuration of the pulse meter 1 is formed of a computer specialized in the function related to timing such as a time function or a chronograph function and the function of detecting the beat, which has a computer main body composed of an MPU 21, a RAM 22, and a ROM 23 as a controller, and is provided with an oscillation circuit 28 for generating a reference clock for operating the controller, and a frequency dividing circuit 29 for generating a clock for timing from the reference clock. Further, as a configuration related to a user interface, there are provided an LCD display device 24 for displaying information on the LCD 4 along the instruction from the MPU 21, an input device 25 for inputting an operation signal, which is input from the operation buttons 5, to the MPU 21, a sound output device 27 for performing sound output of an alarm sound and so on to a piezoelectric speaker 26.

Further, in order for making the computer, which is provided with this hardware configuration, function as the pulse meter, there are provided the pulse wave sensor 8 described above, a body motion sensor 30 for detecting the body motion of a human body, pulse wave signal amplification circuit 31 and body motion signal amplification circuit 32 for respectively amplifying a pulse wave signal from the pulse wave sensor 8 and a body motion signal from the body motion sensor 30, and two channels of A/D conversion circuits (33, 34) for respectively converting the pulse wave signal and the body motion signal, which are amplified via the respective amplifiers (31, 32), into pulse wave signal data and body motion signal data by individually sampling and digitalizing them at every predetermined sampling period. It should be noted that in the present embodiment as the body motion sensor 30 there is used a triaxial acceleration sensor having three axial directions in which the normal direction of the front face of the case 3 is defined as a Z-axis and the direction from 6 o'clock toward 12 o'clock of the watch is defined as a Y-axis as shown in FIG. 2. The X-axis corresponds to a direction perpendicular to these two axial directions, and is substantially identical to the direction from the wrist to the elbow in the state in which the pulse mater 1 is attached.

The MPU 21 executes a predetermined program stored in the ROM 23 in accordance with the operation signal from the input device 25, writes the execution result thereof, data from the A/D conversion circuits (33, 34), and so on into the RAM 22, and further retrieves the data, thus written, from the RAM 22. Further, the MPU 21 controls the LCD display device 24 to display, for example, the information related to the timing function and the execution result of the process on the LCD 4.

In the embodiment described above, a pulse wave signal filtering section and a filter coefficient setting section in the beat detection device as the object of the invention is realized by the MPU 21 processing the pulse wave signal data and the body motion signal data along a predetermined program. For example, a substantial part of the pulse wave signal filtering section is for detecting the beat by eliminating the noise component correlated to the body motion from the pulse wave signal using an adaptive filter formed of, for example, an FIR filter, and the adaptive filter is a digital filter realized by the MPU 21 executing a predetermined program.

Comparative Example to the Invention

Figure 4:
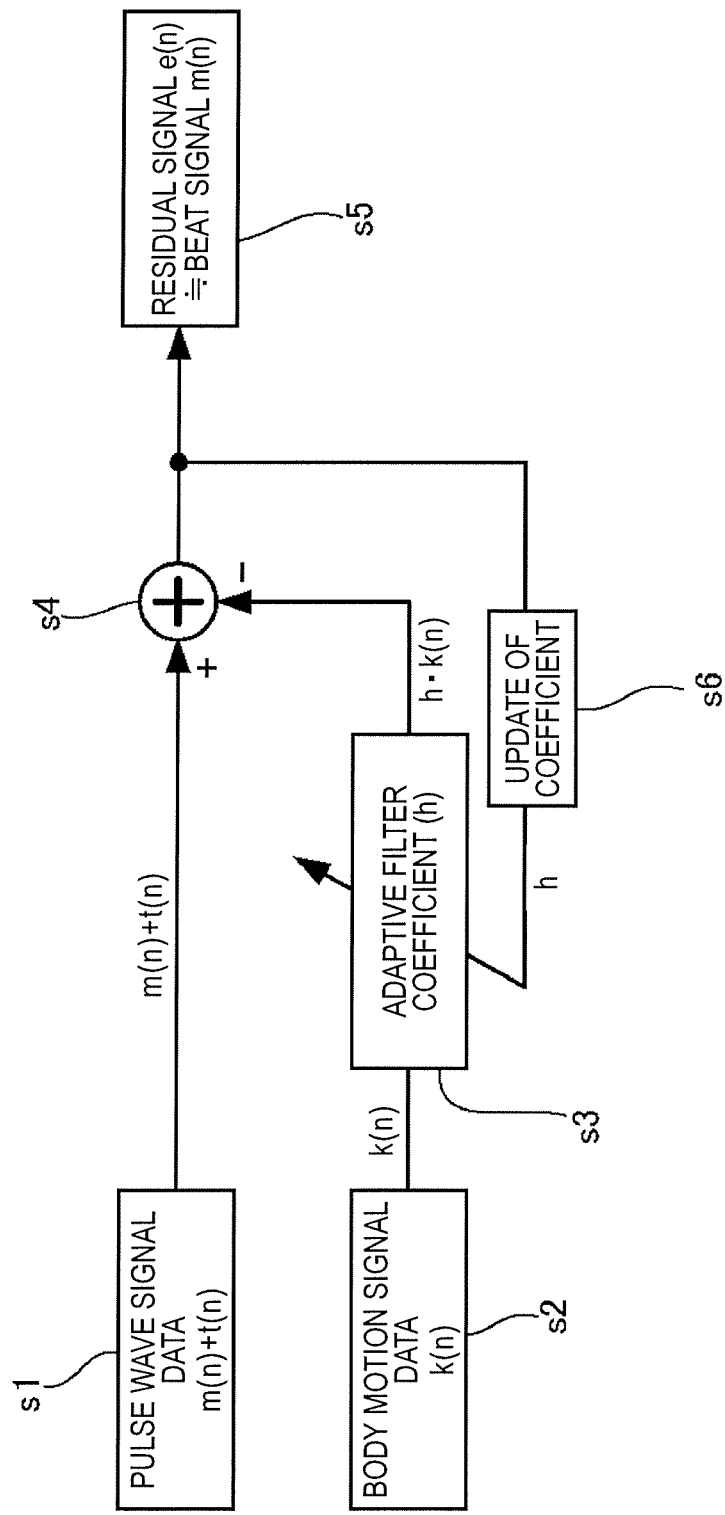
FIG. 4 is a block diagram of a beat detection process in a comparative example to the invention.

Here, as a comparative example to the invention, a typical beat detection algorithm using an adaptive filter will be explained. FIG. 4 shows information processing (the beat detection process) by the beat detection algorithm in the comparative example with blocks corresponding to respective processing steps. It should be noted that in the drawing "n" in each of the signals m(n), t(n), and k(n) represents the data obtained in the nth sampling.

Firstly, the pulse wave signal data p(n) obtained by sampling the pulse wave signal detected by the pulse wave sensor 8 includes the beat signal component m(n) as the object signal to be detected and the noise component t(n) related to the body motion (s1). Therefore, it is arranged that the signal h·k(n) obtained by applying the adaptive filter multiplied the body motion signal data k(n) obtained by sampling the body motion signal from the body motion sensor 30 by a filter coefficient (h) is subtracted (s2 through s4) from the pulse wave signal data p(n) as the body motion-sensitive signal, namely a predicted value of the noise, and the residual signal e(n) is used as the beat signal m(n) (s5).

FIGS. 5A and 5B, and FIGS. 6A and 6B are graphs respectively showing the signal waveform and the frequency analysis result by the fast Fourier transformation (FFT) before and after the signal processing in the beat detection device of the comparative example described above. The curve (41*a* through 41*d*) in the upper part of each of the graphs is a signal waveform obtained by connecting the points obtained by plotting the data in the sampling points in chronological order, and the lateral axes of the graphs are each a time axis. Further, the bar graph (42*a* through 42*d*) below the graph described above shows the frequency analysis result, and the lateral axis represents frequencies. Further, these drawings show the history of trying to detect the beat in the situation in which the body motion changes so as to be increased rapidly, such as a situation in which a human in a resting state rapidly starts to run. It should be noted that the signal waveforms (41*a* through 41*d*) and the frequency analysis results (42*a* through 42*d*) shown in these drawings are those obtained in the same hardware as in the embodiment described above by making the MPU 21 execute the process based on the beat detection process algorithm in the comparative example shown in FIG. 4.

Figure 5A:
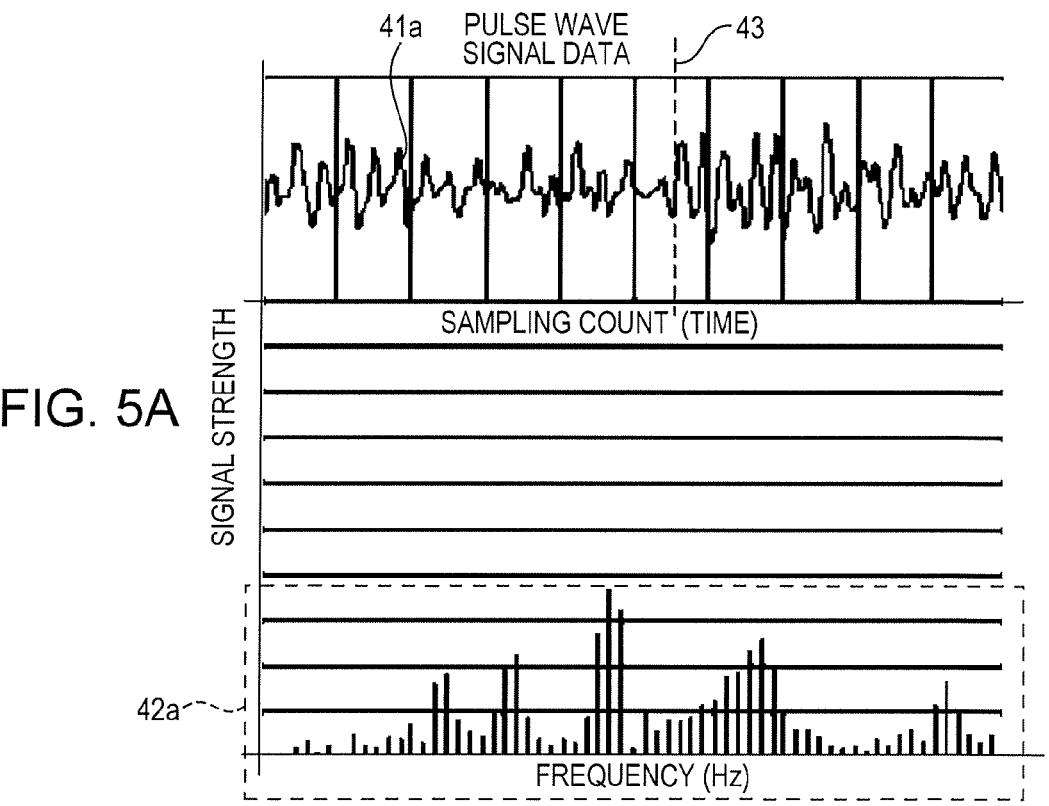
FIG. 5A is a diagram showing data of a pulse wave signal output by a pulse wave sensor constituting the pulse meter described above.
Figure 5B:
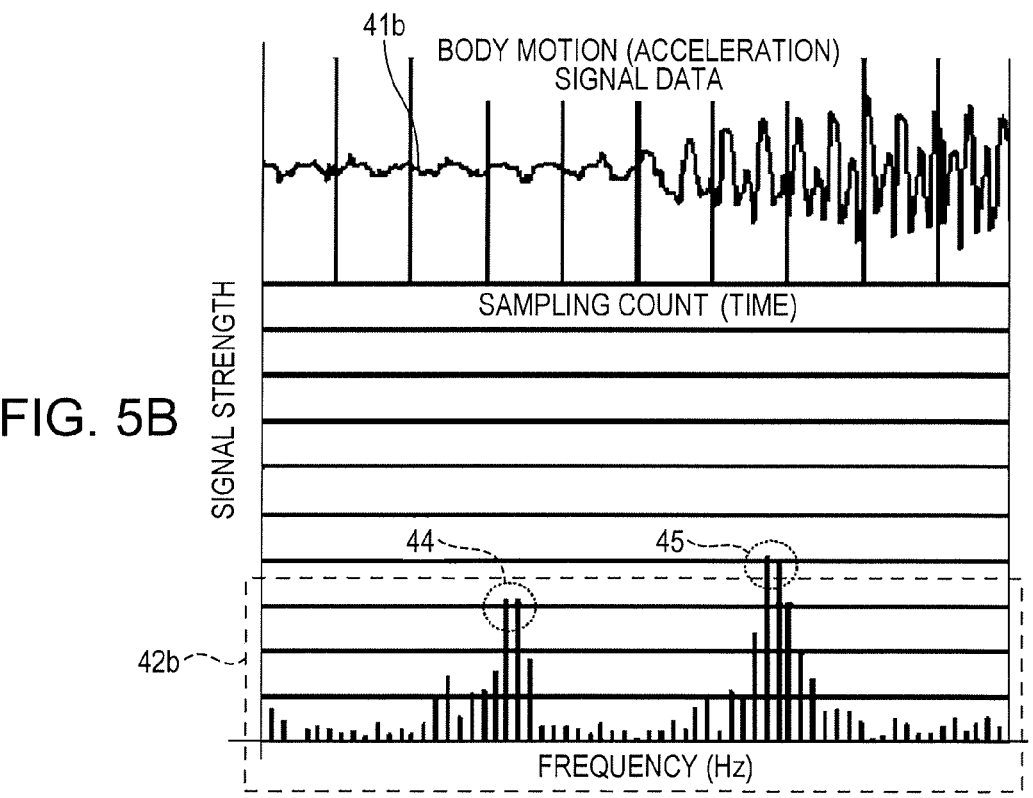
FIG. 5B is a diagram showing data of a body motion signal output by a body motion sensor constituting the pulse meter described above.

Each of the graphs shown in FIGS. 5A, 5B, 6A, and 6B shows the waveforms (41*a* through 41*d*) and the frequency analysis results (42*a* through 42*d*) with respect to the signals obtained for 16 seconds at a sampling frequency of 16 Hz, wherein FIGS. 5A and 5B respectively show the pulse wave signal data output from the pulse wave sensor and the body motion signal data output from the body motion sensor. The noise component derived from the body motion is superposed on the waveform 41*a* of the pulse wave signal data, and it is quite difficult to identify the frequency component representing the beat even from the result 42*a* of the FFT. The waveform 41*b* of the body motion signal data has the amplitude rapidly increased at a certain point 43 due to the change of the body motion in the time-line thereof, and the frequency analysis result 42*b* mainly shows the frequency component (44) due to the body motion change and the harmonic frequency component (45) thereof.

Figure 6A:
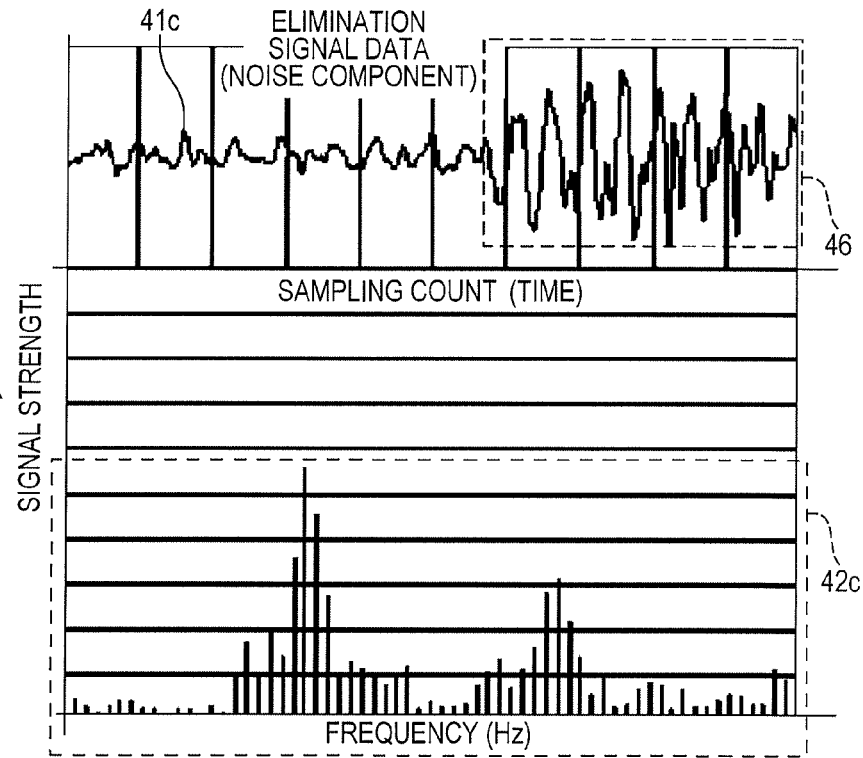
FIGS. 6A and 6B are diagrams respectively showing elimination signal data and beat signal data extracted by the beat detection process of the comparative example described above.
Figure 6B:
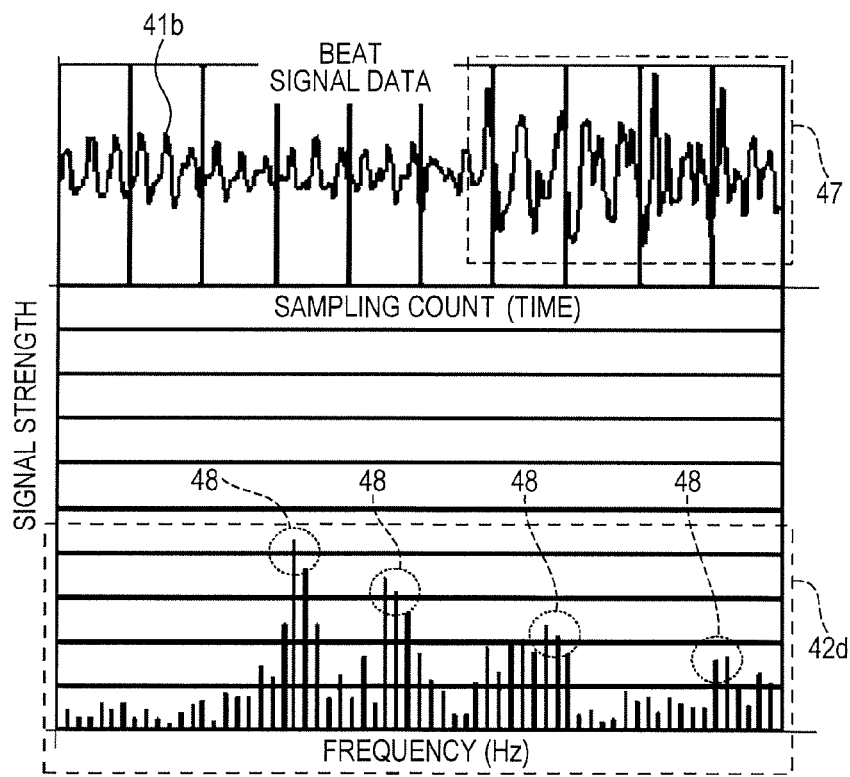

FIG. 6A shows the data of the signal generated from the body motion signal data and the adaptive filter coefficient (h), which is the noise component to be eliminated from the pulse wave signal data shown in FIG. 5A. In the comparative example, the noise component 46 is increased after the body motion has been changed in the waveform 41*c* of the signal data to be eliminated. FIG. 6B shows the signal data obtained by subtracting the elimination signal data from the pulse wave signal data shown in FIG. 5A. In the signal curve 41*d* shown in FIG. 6B, since the noise signal 46, which is included in the elimination signal 41*c* shown in FIG. 6A immediately after the body motion has been changed, and has a large amplitude, is subtracted therefrom, the noise component with the large amplitude is superposed (the reference numeral 47). According to the frequency analysis result 42*d*, there exists a plurality of peaks 48, and it is quite difficult to identify the frequency derived from the heartbeat.

Here, the reason of failing to successfully detect the beat signal in the comparative example will be considered. The coefficient h(n) of the adaptive filter at the update point (n) becomes a value obtained by adding a step count $\mu$ to the coefficient h(n−1) before the update. Specifically, the coefficient h(n) of the adaptive filter is obtained by the following formula.

$$h(n)=h(n-1)+\mu$$

Further, the step count $\mu$ depends on the square of the acceleration Pw describing the strength of the body motion can be expressed as follows, for example, using constants $\alpha$, $\beta$.

$$\mu=\alpha/(\beta+Pw^2)$$

When the body motion is changed to increase, $Pw^2$ is increased, and as a result, $\mu$ becomes to take a small value. Therefore, the reason can be assumed that although the filter coefficient h(n) should be updated to be larger in accordance with the change in the body motion, the difference between the coefficients h(n−1) and h(n) before and after the update becomes small, thus the adaptive filter with the coefficient having a value closer to that of the coefficient thereof before the change in the body motion is applied, and the predicted value of the noise signal fails to follow the actual noise signal after the change in the body motion.

In particular in the case of attaching the beat detection device to the arm in the present embodiment described above, since the way of waving arms is different between the states of the body motion such as the resting state, the walking state, and the running state, it can also be considered that the correlativity between the body motion signal and the noise signal to be eliminated from the pulse wave signal is dramatically changed around the change in the body motion.

At any rate, the graphs shown in FIGS. 5A, 5B, 6A, and 6B are based on the actual measurement values, and there is a fact that in the case in which the body motion is changed so as to be increased significantly, the beat detection device of the comparative example fails to detect the beat signal with accuracy.

Beat Detection Algorithm of the Invention

Figure 7:
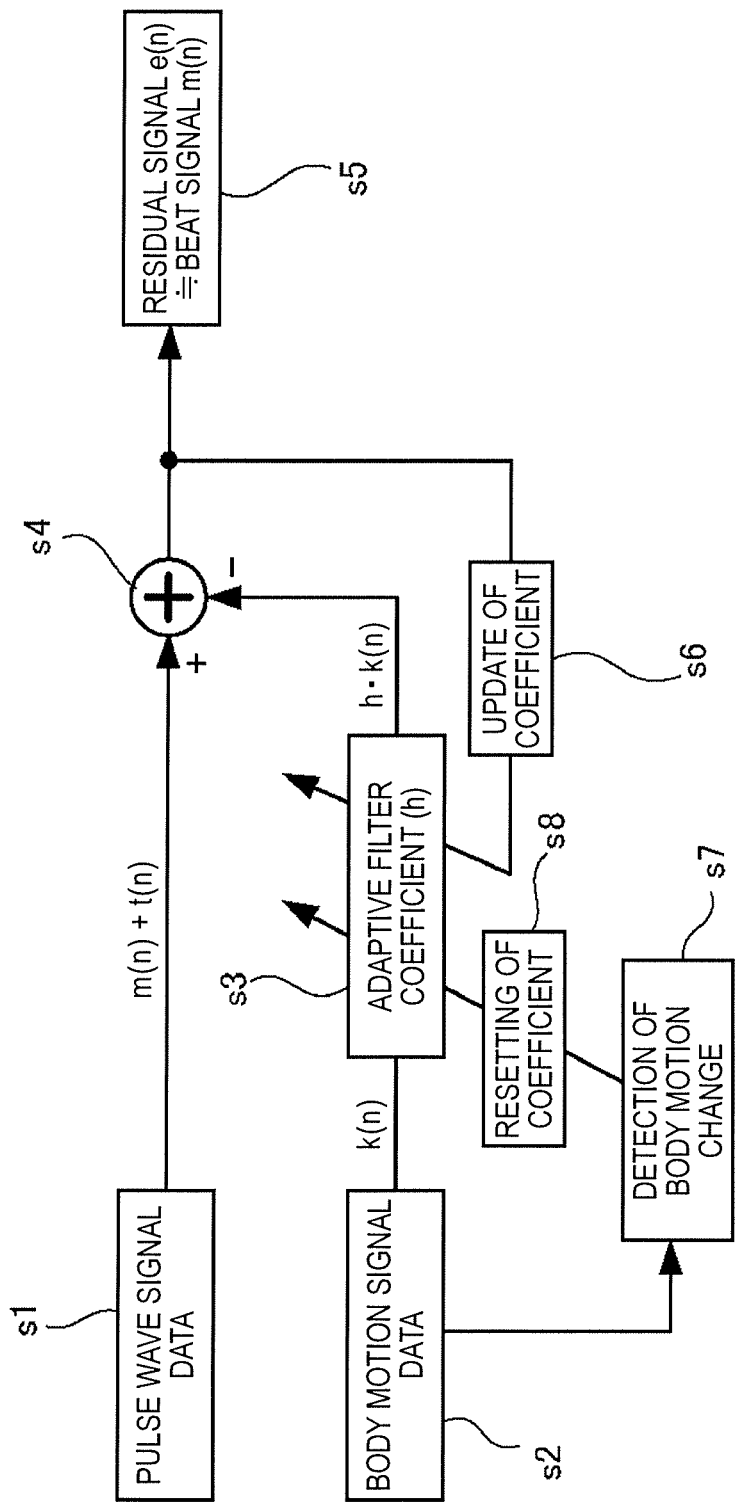
FIG. 7 is a block diagram of a beat detection process according to the invention.

FIG. 7 shows the beat detection process in the beat detection device of the invention with blocks corresponding to the respective processing steps. The beat detection process according to the invention has a feature of including a body motion change detection process s7 for detecting the state in which the body motion is changed so as to increase, and a filter resetting process s8 for forcibly setting the coefficient of the adaptive filter to be a predetermined value when detecting the change in the body motion in addition to the processing steps (s1 through s6) in the comparative example.

In other words, the MPU 21 executes the processing steps (s1 through s6) included in the beat detection process in the comparative example shown in FIG. 4, thereby functioning as a pulse wave signal filtering section, and at the same time, executes the body motion change detection process s7 and the filter reset process s8 in FIG. 7, thereby functioning as a filter coefficient setting section.

Hereinafter, some embodiments thereof will be cited corresponding to the method of detecting the change in the body motion, the processing procedure until the beat is detected, the method of setting the adaptive filter, and so on.

First Embodiment

A first embodiment of the invention is an embodiment related to the method of detecting the change in the body motion, in which the change in the body motion is detected using a band-pass filter, and the coefficient of the adaptive filter is reset to be zero as an initial value when the increasing change in the body motion equal to or greater than a threshold value is detected.

Figure 8A:
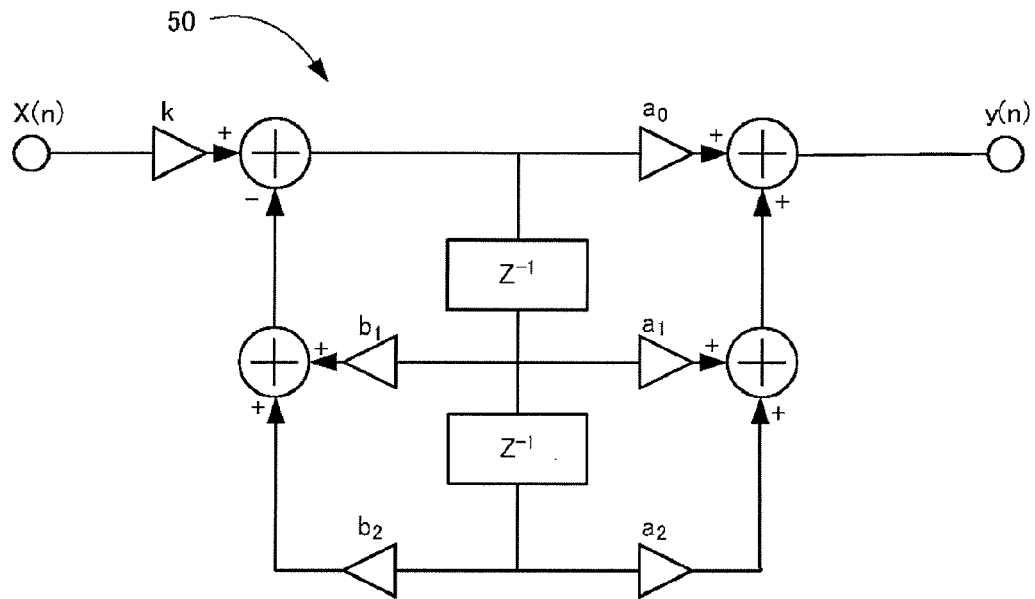
FIG. 8A is a block diagram of a low-pass filter used in the beat detection process in a first embodiment of the invention.
Figure 8B:
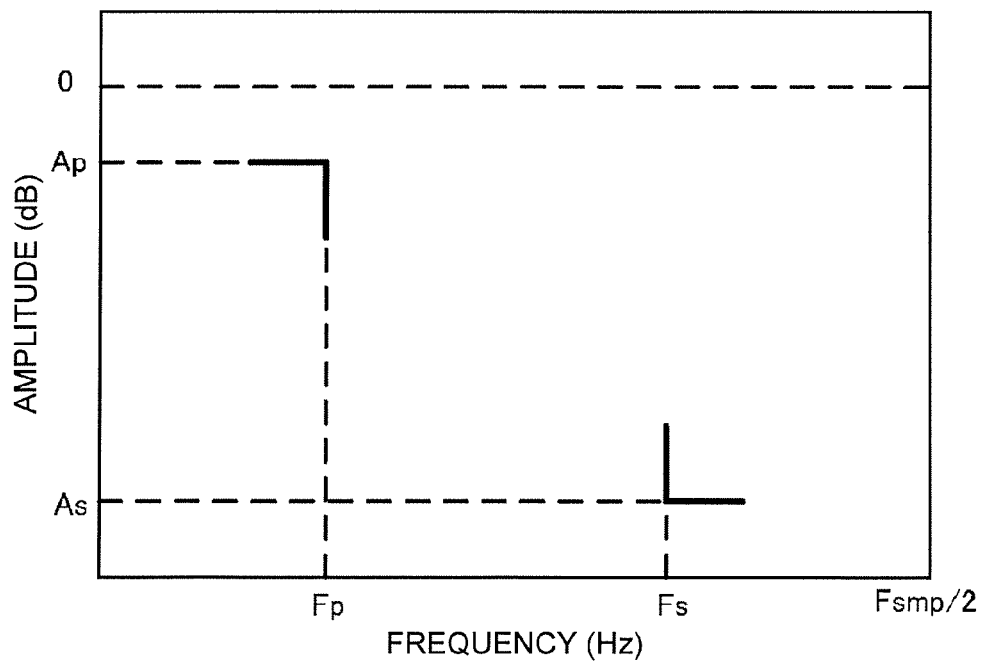
FIG. 8B is a specification diagram of the low-pass filter.

FIGS. 8A and 8B respectively show a block diagram and a specification diagram of the band-pass filter adopted in the body motion change detection method in the first embodiment. As shown in the drawings, in the first embodiment, there is used a single-stage IIR low-pass filter 50. According to the block diagram shown in FIG. 8A, the IIR low-pass filter 50 is expressed as follows denoting a feedforward filter coefficient as a(k), a feedback filter coefficient as b(k), and an input signal and an output signal as x(n), y(n), respectively.

$$y(n)=\{\Sigma a(k) \cdot x(n-k)\}-\{\Sigma b(k) \cdot y(n-k)\}$$

Here, x(n) becomes the body motion signal data, and the low-pass filter process is executed on the body motion signal data, and then the result is output as the body motion signal data y(n). In the specification of the low-pass filter 50, the sampling frequency Fsmp=16 Hz, the band-pass frequency Fp=1 Hz, and the stopband edge frequency Fs=1.5 through 2 Hz are assumed. Further, the passband edge attenuation Ap=3 dB and the stopband edge attenuation As=5 dB are also assumed, resulting in an impaired low-pass filter. Further, in the first embodiment, since the body motion signal data corresponds to acceleration, and has a value the sign of which is switched periodically at a high frequency, the input signal x(n) is the data obtained by squaring the body motion signal data, and the output signal y(n) is obtained by applying the low-pass filter to the data obtained by squaring the body motion signal data when detecting the change in the body motion.

Figure 9A:
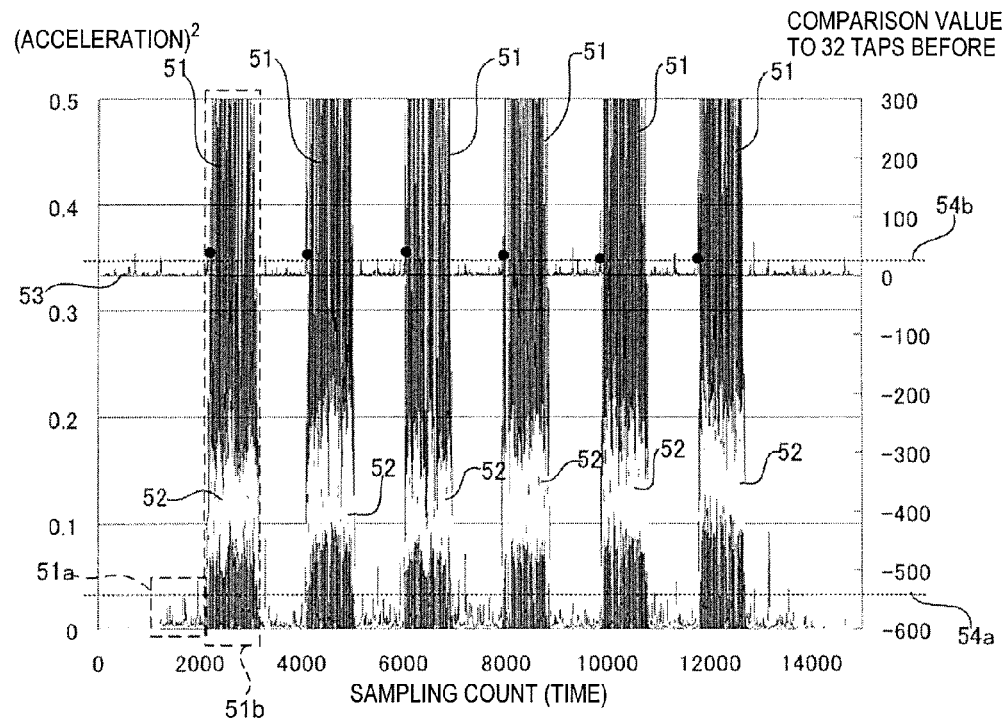
FIGS. 9A and 9B are diagrams showing waveforms of various signal data obtained during the beat detection process of the first embodiment described above.
Figure 9B:
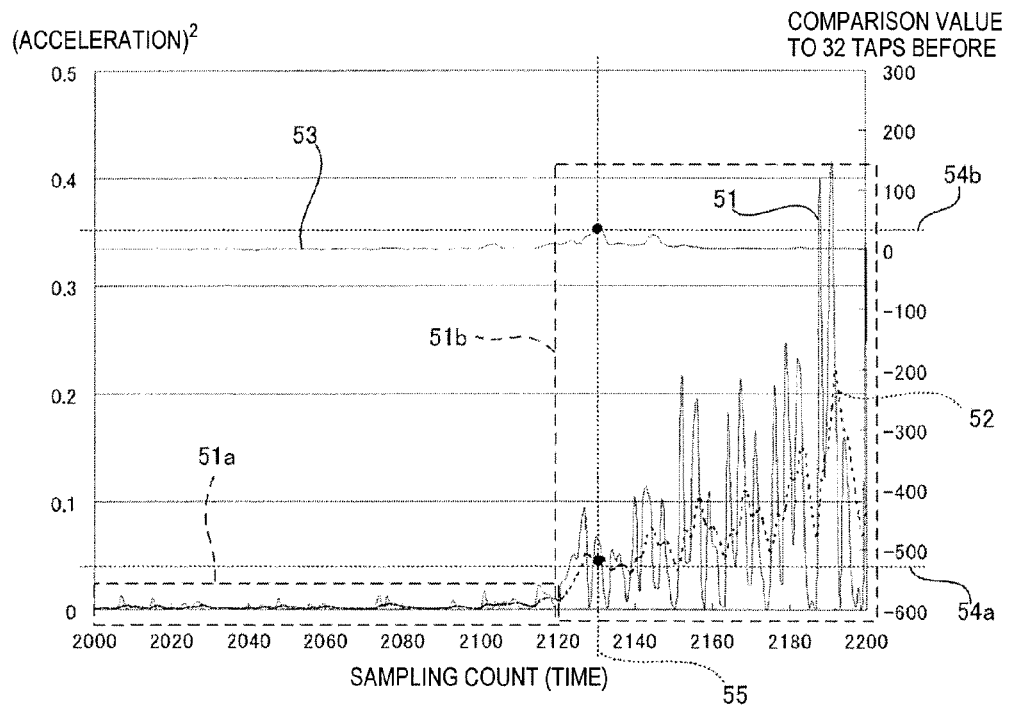

FIGS. 9A and 9B are diagrams for explaining the body motion change detection method according to the first embodiment, and show the square value of the body motion signal data, the body motion signal data to which the low-pass filter described above has been applied, and the ratio between the data at the present moment and the data 32 taps before with respect to the body motion signal data to which the low-pass filter has been applied in the case in which the fluent body motion and the heady body motion such as resting and walking or running, or walking and running are periodically switched. FIG. 9A is a diagram for showing the state in which the body motion is increased or decreased periodically, and it is understood therefrom that in the waveform 51 showing the square of the body motion signal data, the period 51a with a small amplitude and the period 51b with a large amplitude appear periodically. FIG. 9B is a partial enlarged view of FIG. 9A, and enlargedly shows the state before and after the body motion changes so as to increase, namely before and after the transition from the period 51a with the small amplitude to the period 51b with the large amplitude in the squared body motion signal 51.

In order for determining the point of time at which the adaptive filter is initialized to be zero, it is possible to set threshold values (54a, 54b) in both of the body motion signal data 52 to which the low-pass filter has been applied and the ratio data 53 described above, and to determine the point of time when either one or both of the data (52, 53) becomes equal to or greater than the threshold values (54a, 54b) as the reset point of time for initializing the adaptive filter. In the first embodiment, as indicated by the filled circles in the drawings, the point of time at which the both (52, 53) become equal to or greater than the threshold values (54a, 54b) is determined as the reset point 55.

FIGS. 10A and 10B show the result of the signal processing by the beat detection algorithm of the first embodiment. Here, the pulse wave signal data and the body motion signal data before the signal processing are the same as those (41a, 41b) shown in FIGS. 5A and 5B. FIG. 10A shows the waveform 61a and the frequency analysis result 62a of the signal data to be eliminated from the pulse wave signal, and FIG. 10B shows the waveform 61b and the frequency analysis result 62b of the beat signal data obtained by eliminating the signal data described above from the pulse wave signal data shown in FIG. 5A.

In comparison between FIGS. 10A and 10B and the signal processing result in the comparative example shown in FIGS. 6A and 6B, in the first embodiment shown in FIG. 10A, there is no increase in signal strength in the noise component waveform 61a due to the change in the body motion, and is no superposition of the noise signal also in the beat signal data 61b shown in FIG. 10B. Further, a single peak 63 corresponding to the beat is shown in the frequency analysis result 62b, thus the frequency derived from the beat can surely be identified.

Figure 11:
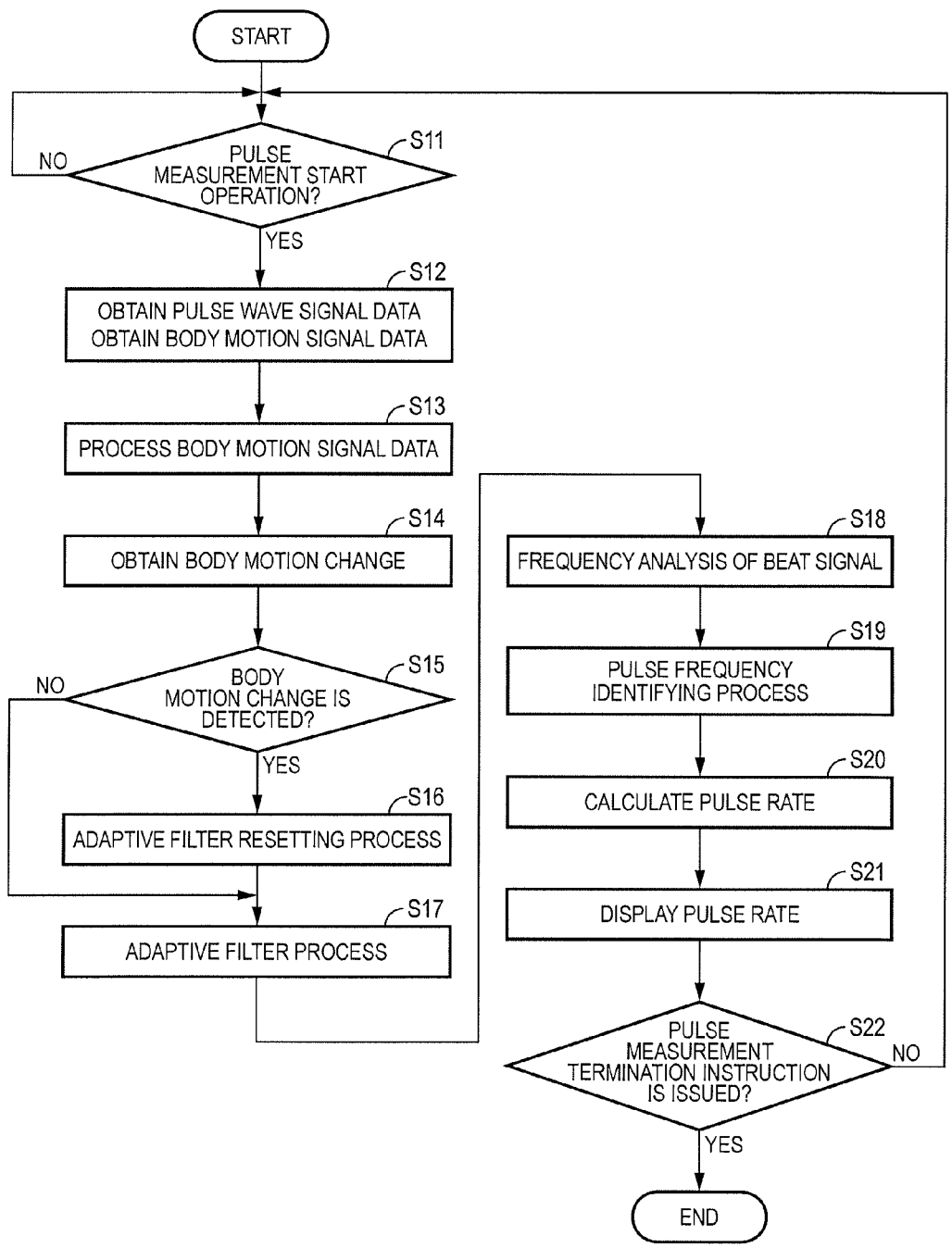
FIG. 11 is a flowchart of a process of the pulse meter described above displaying a pulse rate based on the beat detection process of the first embodiment.

FIG. 11 is a flowchart of a pulse rate display process in the wristwatch pulse meter 1 described above, and shows the flowchart of a process executed by the MPU 21 until the beat signal is extracted by processing the pulse wave signal data and the body motion signal data along the beat detection algorithm of the first embodiment, and finally the pulse rate based on the beat signal is output to and displayed on the LCD.

Firstly, when the user wearing the pulse meter 1 performs a predetermined button operation for starting the pulse measurement, the MPU writes the pulse wave signal data and the body motion signal data into the RAM, thereby obtaining them (s11 to s12). Then, the MPU 21 processes the data with the body motion signal, and obtains the data thus processed as the data representing the state of the change in the body motion (s13, s14). In the first embodiment, the processing process of the body motion signal corresponds to a low-pass filter, and the body motion change state to be obtained is the data obtained by applying the low-pass filter to the data obtained by squaring the body motion signal data.

Subsequently, the MPU 21 refers to the data having been processed, and if the change in the body motion increasing beyond the threshold value is detected, namely if it is detected that the processed data, the ratio data between the value of the processed data at the present moment and the value of the processed data 32 taps before, or both of the processed data and the ratio data are equal to or greater than the threshold values, the MPU 21 resets the coefficient of the adaptive filter to be zero (s15 to s16), and re-creates the adaptive filter from the beginning. Then, the MPU 21 extracts the noise component from the body motion signal data using the adaptive filter thus reset, and at the same time performs the filtering process for eliminating the noise component from the pulse wave signal data, thereby extracting the beat signal data (s17). It should be noted that the ratio data described above can be the data obtained by calculating the difference from, for example, the processed data 32 taps before.

Subsequently, the MPU 21 performs (s18) the FFT on the beat signal data, identifies (s19) the frequency representing the beat, and then calculates (s20) the pulse rate from the frequency. Then, the pulse rate thus calculated is output to and displayed on the LCD 4. Subsequently, the MPU 21 continues (s22 to s1) the series of process (s1 through s21) until the MPU 21 receives the operation information corresponding to the instruction of termination of the pulse measurement by the user.

Figure 12:
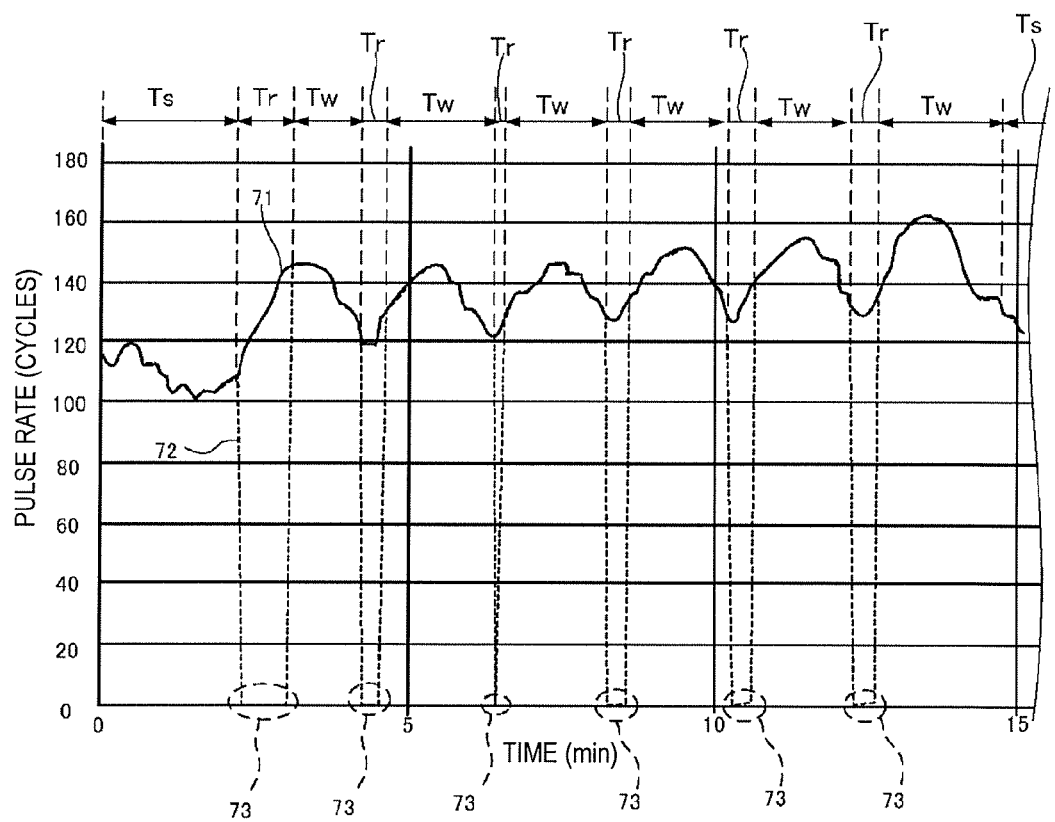
FIG. 12 is a diagram showing the pulse rate measured based on the beat detection process of the first embodiment described above, and the pulse rate measured based on the beat detection process of the comparative example described above.

FIG. 12 is a graph showing the process of the pulse rate display in the wristwatch pulse meter 1, and shows the process thereof in the case in which the beat signal data is detected based on each of the beat detection algorithms of the first embodiment and the comparative example described above to measure the pulse rate.

The two curves shown in the drawing respectively represent a process 71 of the pulse rate measured using the beat detection algorithm in the first embodiment and a process 72 of the pulse rate measured using the beat detection algorithm in the comparative example, and are drawn by plotting the pulse rate displayed on the pulse meter in the condition of periodically providing the period Ts of the resting state, the period Tw of the walking state, and the period Tr of the running state in a period of 15 minutes and when the subject wearing the wristwatch pulse meter 1 changes the body motion along the periods described above.

In the process 72 of the comparative example, the measurement of the pulse rate becomes unsuccessful when the body motion is changed so as to increase, and the display 73 of "zero pulse rate" representing an error appears. In contrast, in the first embodiment, no failure in the measurement due to the body motion change is caused, and it is possible to continue to measure the pulse rate with accuracy.

Second Embodiment

A second embodiment of the invention is also the embodiment related to the method of detecting the body motion change, and is for detecting the body motion change based on the summed value of the body motion signals having been output for a past predetermined period of time. Further, if it is detected that the body motion change increases beyond a predetermined threshold, the coefficient of the adaptive filter is initialized to be zero. In the present embodiment, it is possible to use the value obtained by accumulating the values of the body motion signal data obtained in the respective sampling opportunities of a past predetermined number of times, or the moving average deviations obtained by dividing the value obtained by the accumulation by the number of times of the sampling opportunities, as the data for detecting the body motion change. It should be noted that also in the present embodiment, the value obtained by squaring the body motion signal data is used when detecting the body motion change. Then, the moving average is obtained with respect to the square value of the body motion signal data.

Figure 13A:
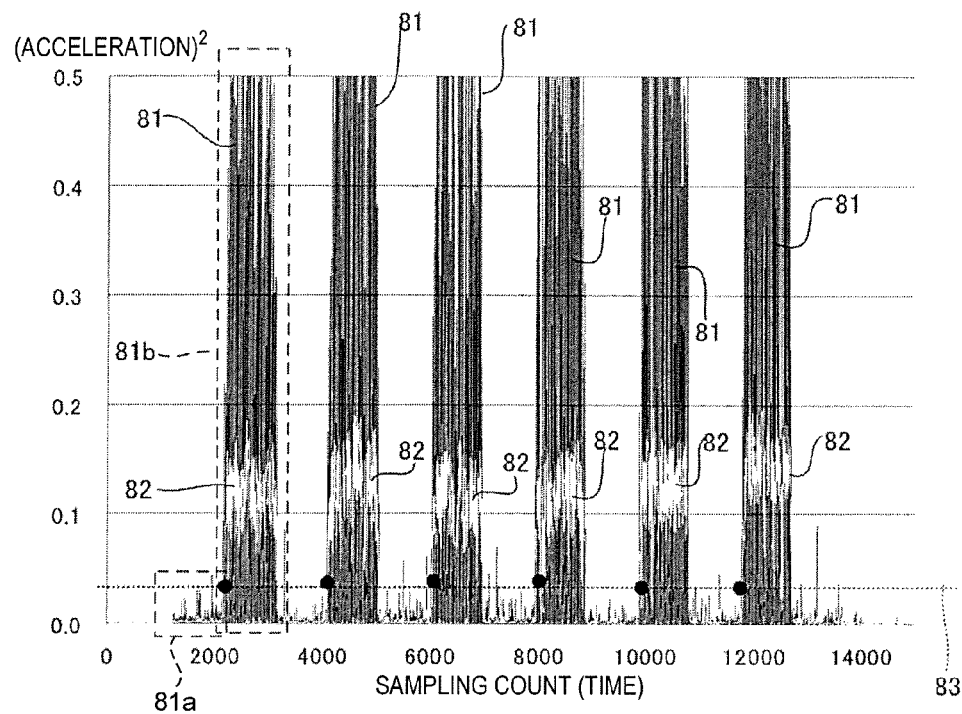
FIGS. 13A and 13B are diagrams showing waveforms of various signal data obtained during the beat detection process of a second embodiment of the invention.
Figure 13B:
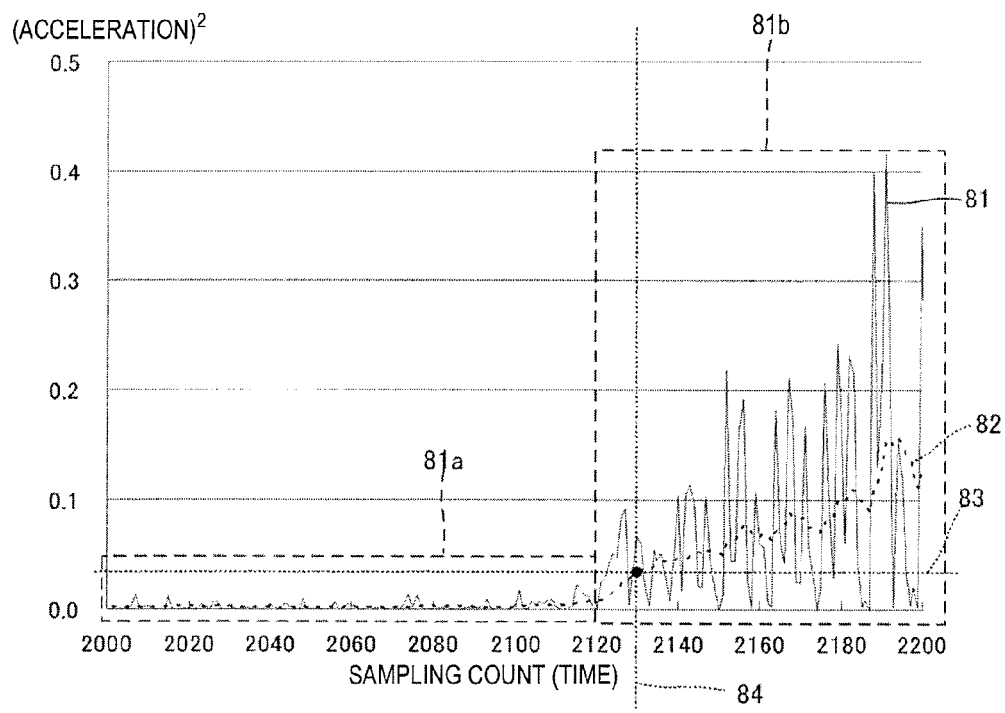

FIGS. 13A and 13B are explanatory diagrams of the body motion change detection method in the second embodiment, and show the waveform of the body motion signal data and the process of the moving average corresponding to past 16 times of sampling of the body motion signal data. Similarly to FIGS. 9A and 9B, there are shown the states (81a, 81b) of the body motion signal data 81 in which the body motion is periodically increased or decreased, wherein FIG. 13A shows the long-term processes of the body motion signal data 81 and the moving average 82 of the data. FIG. 13B is a partial enlarged view of FIG. 13A, and enlargedly shows the states before and after (81a, 81b) the body motion is changed so as to increase. Further, in the second embodiment, the threshold value 83 is provided for the moving average, and the points of time at which the moving average exceeds the threshold value 83 are detected as the reset points 84 indicated by the filled circles in the drawing.

Third Embodiment

A third embodiment of the invention is an embodiment related to the method of detecting the body motion change similarly to the first and second embodiments described above. In the present embodiment, the body motion change is detected based on the amplitude of the body motion signal data. Further, the points of time at which the amplitude thereof exceeds a predetermined threshold value are determined as the reset points.

Figure 14A:
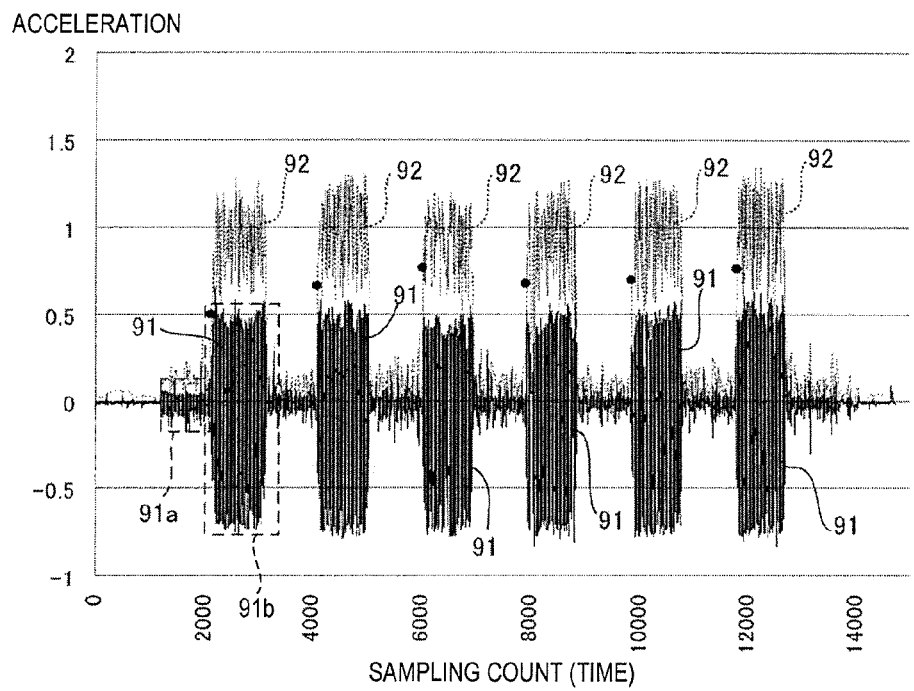
FIGS. 14A and 14B are diagrams showing waveforms of various signal data obtained during the beat detection process of a third embodiment of the invention.
Figure 14B:
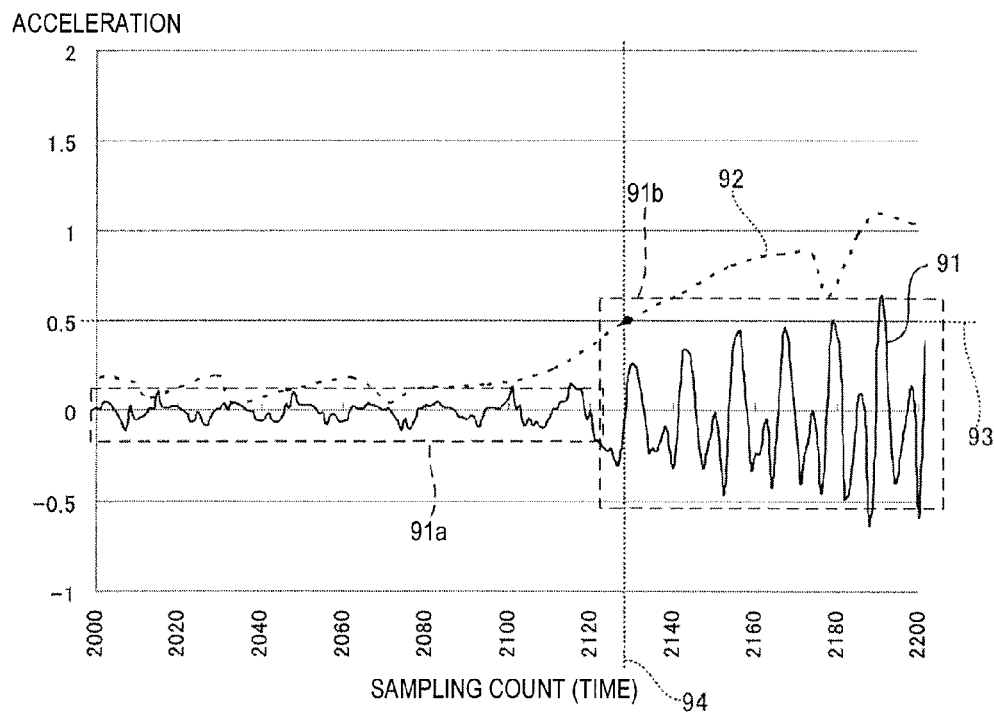

FIGS. 14A and 14B show explanatory diagrams of the body motion change detection method according to the third embodiment. The drawings show the process of the body motion signal data 91 and the process of the absolute value 92 of the amplitude corresponding to the state in which the body motion is periodically increased or decreased, wherein FIG. 14A shows the long-term body motion signal data 91 and the absolute value 92 of the amplitude, and FIG. 14B is a partial enlarged view of FIG. 14A, and enlargedly shows the states before and after (91a, 91b) the body motion is changed so as to increase. Also in this case, as indicated by the filled circles in the drawings, the points of time at which the absolute value 92 of the amplitude exceeds a predetermined threshold value 93 are determined as reset points 94.

Fourth Embodiment

Incidentally, the direction of the body motion is not limited to one. Therefore, there is a possibility that the noise is not eliminated successfully unless the body motion sensor is implemented so as to detect the body motion in the direction having the most significant influence on the noise. A fourth embodiment relates to the beat detection process designed in consideration of such a possibility.

In the fourth embodiment, a body motion sensor detecting the body motion in at least two axial directions is used, and firstly the beat signal is extracted based on the body motion signal in the axial direction having the most significant influence on the body motion, and then this beat signal is used as the new pulse wave signal, and the body motion signal having the second most significant influence thereon is eliminated as the noise component. By sequentially eliminating the body motion signals in two axial directions or three axial directions in the manner as described above, it becomes possible to finally detect the correct beat.

Figure 15:
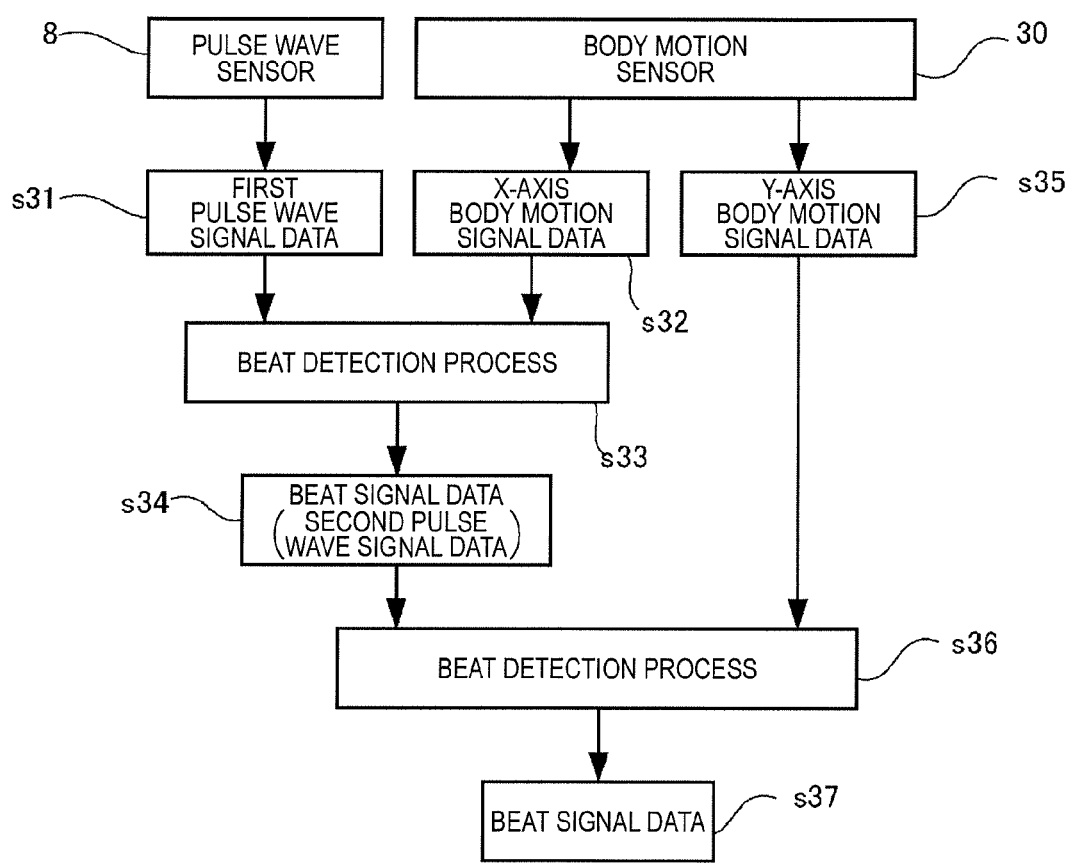
FIG. 15 is a schematic diagram of the beat detection process of a fourth embodiment of the invention, which is a diagram showing a procedure of a process of eliminating noise components in two axial directions individually from the data of the pulse wave signal described above.
Figure 16:
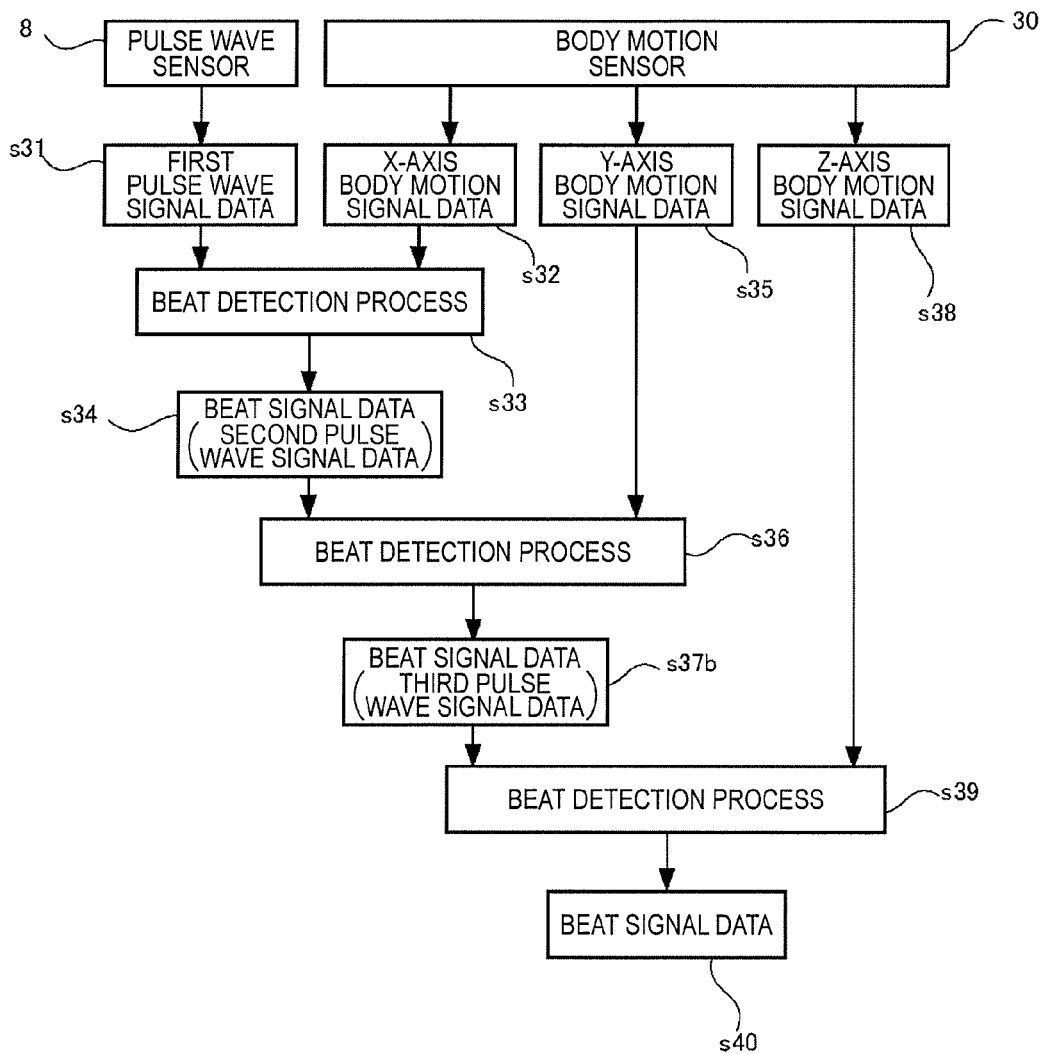
FIG. 16 is a schematic diagram of the beat detection process of a fourth embodiment of the invention, which is a diagram showing a procedure of a process of eliminating noise components in three axial directions individually from the data of the pulse wave signal described above.

FIGS. 15 and 16 show the beat detection processing procedure in the fourth embodiment. FIG. 15 shows the processing procedure for eliminating the noise components in two axial directions, and FIG. 16 shows the processing procedure for eliminating the noise components in three axial directions. Further, it is assumed in these drawings that the axis having the most significant influence on the body motion is an x-axis, and the influence thereof in a y-axis and a z-axis decreases in this order. As shown in FIG. 15, in the case of eliminating the noise components in the two axial directions, the beat signal detection process (s33) shown in FIG. 7 is performed using the pulse wave signal data (a first pulse wave signal data; s31) based on the pulse wave signal from the pulse wave sensor 8 and the body motion signal data (s32) in the x-axis direction, then the beat signal data thus extracted as a result is set as a second pulse wave signal data (s34), then the beat detection process is performed again (s36) using the second pulse wave signal data and the body motion signal data (s35) in the y-axis direction, and then the beat signal data output as a result is adopted (s37) as the final beat signal data.

In the case in which the body motion signals in all of the three axial directions, the final beat signal data (s37) shown in FIG. 15 is set (s37b) as the third pulse wave signal data, then the third beat detection process is performed (s39) using the third pulse wave signal data and the body motion signal data s38 in the z-axis direction, and then the beat signal data thus extracted by the process s39 is set (s40) as the final beat signal data.

It should be noted that since in the embodiments described above, namely the beat detection device of the wristwatch pulse meter 1, the usage thereof is detection pulse measurement in walking or jogging, the body motion signal is mainly influenced by the way of waving the arm and the speed thereof. According to the finding through experiments and so on, in the three axial directions shown in FIG. 2, the axial direction the most significantly influenced by the way of waving the arm is the x-axis direction, what is the second most significantly influenced is the y-axis direction, and the z-axis direction is hardly influenced in the assumed usage. Therefore, in the beat detection device of the type attached to the arm, it is preferable to process the body motion signal data in the x-axis, y-axis, and z-axis in this order.

OTHER EMBODIMENTS

Coefficient Reset Into Adaptive Filter

Although in the first through third embodiments described above the coefficient of the adaptive filter is reset to be zero when detecting the fact that the body motion is changed so as to increase beyond the threshold value, it is sufficient for the coefficient to have a predetermined value with which the noise derived from the body motion can be extracted. For example, the coefficient is previously prepared in accordance with each of the predetermined body motion states such as the resting state, the walking state, and the running state, and in the case in which it is detected that the body motion change is increased beyond the predetermined threshold value, and at the same time the change corresponds to a predetermined body motion change (e.g., the change from the walking state to the running state), the coefficient of the body motion adaptive filter is reset to be the value corresponding to the body motion after the change. The noise component can effectively be extracted also in such a process as described above. It should be noted that in order for identifying the state of the body motion, it is possible to refer to the amplitude of the body motion signal data.

Resetting Interval of Adaptive Filter Coefficient

If the coefficient of the adaptive filter is reset to be zero, for example, every time the body motion change is increased beyond the threshold value, the load on the hardware is increased due to the resetting process, which might pose a problem for other processes. For example, since the pulse meter obtains the pulse rate at the present moment from the beat signal data corresponding to a past predetermined period, if the resetting process is performed frequently, the pulse meter is required to frequently recount the pulses again from the point of time at which the resetting process is performed. Thus, the real-time display of the pulse rate is hindered.

Therefore, it is preferably arranged that the resetting of the coefficient is inhibited for a predetermined period after resetting the coefficient of the adaptive filter to be zero or other predetermined coefficient values. The inhibition period for the resetting process can be measured using a real-time clock incorporated in the MPU, or can be measured by multiplying the sampling cycle time by the number of times of sampling. Further, in the case of using the real-time clock, it is possible to start a decrement timer in which a predetermined remaining period is set using the point of time at which the coefficient is reset as the starting point. In the case of using the sampling period and the number of times of sampling, it is possible to previously store a predetermined number of times of sampling in, for example, the ROM, and to stop the resetting process of the coefficient of the adaptive filter from the point of time of resetting the coefficient and until the sampling data such as the pulse wave signal data or the body motion signal data is input a predetermined number of times.

The invention can be applied to any device for outputting information related to the beat of the human body, and can be used in any device treating biological information such as a device for outputting and displaying a temporal change in the beat with a waveform and so on such as a pulse meter, a blood-pressure meter, or an electrocardiographic monitor.

Japanese Patent Application No. 2009-021236 filed on Feb. 2, 2009, is hereby incorporated by reference in its entirety.

What is claimed is:

1. A beat detection device comprising:
   a pulse wave sensor adapted to detect and output a pulse wave signal;
   a body motion sensor adapted to detect and output a body motion signal due to a body motion of a human body;
   a filtering section adapted to remove a noise signal in the pulse wave signal using the body motion signal; and
   a filter setting section adapted to set a coefficient of the filtering section to a predetermined value, the filter setting section resetting the coefficient of the filtering section to be an initial value in response to detection of a change of the body motion signal beyond a predetermined threshold value during processing of the pulse wave signal.

2. The beat detection device according to claim 1,
wherein the filter setting section is adapted to store, in a memory, a first coefficient corresponding to a first type of body motion states of a user, and a second coefficient corresponding to a second type of the body motion states of the user, the second type being different from the first type, the first coefficient and the second coefficient being previously set for the first type and the second type, respectively, wherein the filter setting section is adapted to set the coefficient of the filtering section to the second coefficient in response to detection of the change of the body motion signal exceeding the predetermined threshold value and the change of a type of the body motion states from the first type to the second type.

3. The beat detection device according to claim 1, wherein the body motion sensor outputs body motion signals in at least two axial directions, and the filtering section sequentially removes the noise signal in the pulse wave signal using the body motion signals in at least the two axial directions in a predetermined order.

4. The beat detection device according to claim 3, wherein the beat detection device is configured to be attached to an arm, and the body motion sensor outputs body motion signals corresponding to a direction from a wrist toward an elbow as a first axial direction to be primarily removed from the pulse wave signal, and to a direction perpendicular to the direction from the wrist toward the elbow and parallel to the ground in case where the arm extends in parallel to a ground and a palm connected to the arm is parallel to the ground, as a second axial direction to be secondary removed from the pulse signal.

5. The beat detection device according to claim 1, wherein the filter setting section detects the change of the body motion signal beyond the predetermined threshold value based on a signal obtained by applying a band-pass filter on the body motion signal.

6. The beat detection device according to claim 1, wherein the filter setting section detects the change of the body motion signal beyond the predetermined threshold value based on a summed value of the body motion signal output in a past predetermined period.

7. The beat detection device according to claim 1, wherein the filter setting section detects the change of the body motion signal beyond the predetermined threshold value based on an amplitude of the body motion signal output in a past predetermined period.

8. The beat detection device according to claim 1, wherein the filter setting section avoids the resetting of the coefficient of the filtering section in response to a second detection of the change of the body motion signal beyond the predetermined threshold value during the processing of the pulse wave signal until a predetermined period of time elapses after resetting the coefficient of the filtering section in response to the first detection, and resets the coefficient of the filter section after the predetermined period of the time elapses.

9. The beat detection device according to claim 8, further comprising a clock timer configured to measure the predetermined period of the time, the clock timer commencing to count the predetermined period of the time at a timing of resetting of the coefficient of the filtering section in response to the first detection.

10. The beat detection device according to claim 1, further comprising:
a pulse measurement section adapted to measure a pulse rate based on the pulse wave signal; and
a display section adapted to display the pulse rate.

11. A beat detection method comprising:
performing pulse wave detection process for outputting a pulse wave signal by a pulse wave sensor;
performing body motion detection process for outputting a body motion signal due to a body motion of a human body by a body motion sensor;
performing filtering process for removing a noise signal in the pulse wave signal using the body motion signal by a filtering section; and
performing coefficient setting process for setting a coefficient of the filtering section to a predetermined value, the performing coefficient setting process including resetting the coefficient of the filtering section to be an initial value in response to detection of a change of the body motion signal beyond a predetermined threshold value during processing of the pulse wave signal by a filtering setting section.

* * * * *